US010531820B2

(12) United States Patent
De Haan et al.

(10) Patent No.: US 10,531,820 B2
(45) Date of Patent: Jan. 14, 2020

(54) DEVICE, SYSTEM AND METHOD FOR DETERMINING THE CONCENTRATION OF A SUBSTANCE IN THE BLOOD OF A SUBJECT

(71) Applicant: KONINKLIJKE PHILIPS N.V., Eindhoven (NL)

(72) Inventors: Gerard De Haan, Helmond (NL); Mukul Rocque, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1087 days.

(21) Appl. No.: 14/941,934

(22) Filed: Nov. 16, 2015

(65) Prior Publication Data

US 2016/0143567 A1    May 26, 2016

Related U.S. Application Data

(60) Provisional application No. 62/083,338, filed on Nov. 24, 2014.

(51) Int. Cl.
*A61B 5/1455* (2006.01)
*A61B 5/1495* (2006.01)
*A61B 5/00* (2006.01)

(52) U.S. Cl.
CPC .......... *A61B 5/1495* (2013.01); *A61B 5/1455* (2013.01); *A61B 5/6887* (2013.01); *A61B 5/7271* (2013.01); *A61B 2576/00* (2013.01)

(58) Field of Classification Search
CPC . A61B 5/1495; A61B 5/0077; A61B 5/02416; A61B 5/14551; A61B 5/7203
See application file for complete search history.

(56) References Cited

U.S. PATENT DOCUMENTS

| 4,621,643 A * | 11/1986 | New, Jr. ............. A61B 5/14552 250/252.1 |
| 6,385,471 B1 | 5/2002 | Mortz |

(Continued)

FOREIGN PATENT DOCUMENTS

| WO | 2007/122375 | 11/2007 |
| WO | 2013/030739 | 3/2013 |

(Continued)

OTHER PUBLICATIONS

Suzaki et al., "Non-Invasive Measurement of Total Hemoglobin Deratives using Multiwavelength Pulse Spectrophotometry", IEEE, 28th EMBS Conf, 2006 (Year: 2006).*

(Continued)

*Primary Examiner* — Eric F Winakur

(57) ABSTRACT

In a device, system and method for determining the concentration of a substance, such as the oxygen saturation in the blood of a subject, the influence of specular reflection is reduced or removed. An input unit is configured to receive detection signals reflected back from a skin area of the subject in response to irradiation of the skin area by a radiation signal. A signal extraction unit is configured to extract at least two photo-plethysmography, PPG, signals at two different wavelengths from the detection signals. A processing unit is configured to compute the concentration of a selected substance in the blood of the subject based on the PPG signals taking into account a skin tone of the subject.

14 Claims, 3 Drawing Sheets

(56) References Cited

U.S. PATENT DOCUMENTS

2007/0043269 A1\* 2/2007 Mannheimer ...... A61B 5/14551
600/323
2009/0024041 A1\* 1/2009 Cho ..................... A61B 5/0059
600/476

FOREIGN PATENT DOCUMENTS

| WO | 2013/038326 | 3/2013 |
|----|-------------|--------|
| WO | 2013/046082 A2 | 7/2013 |
| WO | 2013/046082 A3 | 7/2013 |
| WO | 2014/068436 A1 | 5/2014 |

OTHER PUBLICATIONS

Humphreys et al., "Noncontact Simultaneous Dual Wavelength PPG", Review of Scientific Instruments 78, 044304, pp. 1-6, 2007 (Year: 2007).\*

Wieringa et al., "Contactless Multiple Wavelength PPG Imaging", Annals of Biomedical Engineering, vol. 33, No. 8, pp. 1037-1041, 2005 (Year: 2005).\*

Pratik Sahindrakar, "Improving Motion Robustness of Contact-less Monitoring of Heart Rate Using Video Analysis", Eindhoven University of Technology, Aug. 24, 2011.

Walter Karlen, "Detection of the Optimal Region of Interest for Camera Oximetry" 2013.

Chen Tong, "Hyperspectral Imaging for the Remote Sensing of Blood Oxygenation and Emotions" 2012.

\* cited by examiner

DEVICE, SYSTEM AND METHOD FOR DETERMINING THE CONCENTRATION OF A SUBSTANCE IN THE BLOOD OF A SUBJECT

CROSS REFERENCE TO RELATED APPLICATIONS

This application claims the benefit of U.S. Provisional application No. 62/083,338 filed Nov. 24, 2014, and European patent application no. 114194509.7 filed Nov. 24, 2014, all of which are incorporated herein by reference.

FIELD OF THE INVENTION

The present invention relates to a device, system and method for determining the concentration of a substance, such as the concentration of oxygen (oxygen saturation, SpO2), bilirubin, CO2, etc., in the blood of a subject, such as a person or animal.

BACKGROUND OF THE INVENTION

Vital signs of a person, for example the heart rate (HR), the respiration rate (RR) or the arterial blood oxygen saturation (SpO2), serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow.

Fast and reliable detection and analysis of a pulse signal and oxygen saturation level (SpO2) is one of the most important activities in many healthcare applications, which becomes crucial if a patient is in a critical condition. In those situations, pulsatility of a heart beat signal is very weak, and therefore, the measurement is vulnerable to any sort of artifacts.

Modern photoplethysmography sensors do not always provide fast and reliable measurement in critical situations. For instance, contact finger pulse oximeters (based on transmissive PPG) are vulnerable to motion of a hand, and fails in case of centralization of a patient due to lower blood volumes on body peripherals. Contact forehead pulse oximeter sensors (using a reflective PPG measurement mode) are supposed to be more robust to a centralization effect. However, the accuracy, robustness and responsiveness of a forehead sensor depends heavily on correct positioning of a sensor on a forehead and proper pressure applied to a skin (too tight application of a sensor might reduce a local blood pulsatility, too loose application might lead to non-reliable measurements due to motion artifacts and/or venous pulsatility).

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as NICU patients with extremely fragile skin or premature babies.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Wieringa, et al., "Contactless Multiple Wavelength Photoplethysmographic Imaging: A First Step Toward "SpO2 Camera" Technology," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Specular reflectance of light from the skin's surface causes calibration errors leading to incorrect measurement of the concentration of various substances, such as SpO2, CO2, bilirubin, etc. in the subject's blood. Current ideas necessitate the use of polarizers in the measurement setup which are difficult to align and prove to make for a difficult setup in practice.

WO 2013/030739 A1 discloses a system and method for extracting information from detected characteristic signals.

The system comprises an interface for receiving a data stream derivable from electromagnetic radiation reflected by an object, the data stream comprising a continuous or discrete characteristic signal including physiological information and a disturbing signal portion, the physiological information being representative of at least one at least partially periodic vital signal, the disturbing signal portion being representative of at least one of an object motion portion and/or a non-indicative reflection portion, the characteristic signal being associated with an additive signal space, the signal space comprising additive channels for representing the characteristic signal. The system further comprises a converter means for transferring the characteristic signal by converting at least three absolute components of the characteristic signal related to respective additive channels to at least two difference components of the characteristic signal, wherein each of the at least two difference components can be derived through a respective arithmetic transformation considering at least two of the at least three absolute components, wherein the arithmetic transformation comprises additive and subtractive coefficients, the disturbing signal portion being at least partially suppressed in the transferred signal. The system additionally comprises an extractor means for extracting the vital signal from the transferred signal, and preferably the vital signal is extracted under consideration of an additive or subtractive expression or a ratio of the at least two difference components.

SUMMARY OF THE INVENTION

It is an object of the present invention to provide a device, system and method for determining the concentration of a substance in the blood of a subject that remove or at least reduce the influence of specular reflectance.

In a first aspect of the present invention a device for determining the concentration of a substance in the blood of a subject is presented comprising an input unit configured to receive detection signals reflected back from a skin area of the subject in response to irradiation of the skin area by a radiation signal, a signal extraction unit configured to extract at least two photo-plethysmography, PPG, signals at two different wavelengths from said detection signals, and a processing unit configured to compute the concentration of a desired substance in the blood of the subject based on said PPG signals, wherein said computation is adapted to the skin tone of the subject.

In a further aspect of the present invention a corresponding method is presented.

In a still further aspect of the present invention a system for determining the concentration of a substance in the blood of a subject is presented comprising a radiation detection unit configured to detect detection signals reflected back from a skin area of the subject in response to irradiation of the skin area by a radiation signal, and a device as disclosed herein configured to determine the concentration of a substance in the blood of the subject from said detection signals.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed device and as defined in the dependent claims.

The present invention is based on the finding that the fraction of specular reflection (of total reflected light) can be very different between the wavelengths, particularly for subjects with a dark skin-tone (where the diffusely reflected part of shorter wavelengths may be strongly absorbed (or, more precisely, strongly reduced), while the specular reflection remains equally strong as for longer wavelengths of the total reflected light). Consequently, even a constant specular reflection across different wavelengths will lead to a calibration error depending on the skin tone of the subject. Particularly, subjects with a very dark skin can have significantly stronger absorption of the red light compared to the infrared light, while subjects in general have very similar skin reflectance in infrared light.

Hence, since the specular reflection causes the calibration to be different for subjects with different skin-tones, it is proposed to adapt the computation of the concentration of the substance in the blood of the subject, in particular by adapting the calibration, to the recorded skin-tone. In preferred embodiments the computation involves determining the ratio of the pulsatilities, i.e. the amplitudes of the normalized PPG-signals. Thus, for adaption of the computation of the concentration a property (e.g. the amplitude) of the signals is being used and modified.

In a preferred embodiment said processing unit is configured to adapt the computation to the relative mean reflection of radiation from said skin area at said two different wavelengths. For instance, the estimated pulsatility or the estimated amplitude of the (normalized) PPG signals may be adapted. In yet other implementation the normalization is adapted prior to measuring the pulsatility.

In another embodiment it is proposed that the skin tone is estimated with another device/sensor as part of the proposed system, wherein the output of this device/sensor is used to adapt the computation.

Preferably, particularly in an embodiment for determining the arterial blood oxygen saturation (SpO2), said processing unit is configured to form a ratio of a first normalized pulsatility at a first wavelength and a second normalized pulsatility at a second wavelength for the computation of the concentration, wherein the denominator of the first and/or the second normalized pulsatility is corrected by a correction factor.

The processing unit may be configured to use as a correction factor used for correcting the denominator of the first normalized pulsatility a fraction of the DC level of the PPG signal at the second wavelength and/or to use as a correction factor used for correcting the denominator of the second normalized pulsatility a fraction of the DC level of the PPG signal at the first wavelength. In another embodiment the processing unit may be configured to use as correction factor for correcting the denominator of the first normalized pulsatility at a wavelength in the red spectrum a fraction of the DC level of the PPG signal at a wavelength in the infrared spectrum.

In still another embodiment said processing unit is configured to use as a correction factor a fraction in the range of 5% to 15%, in particular 10% of the DC level of the PPG signal at a wavelength in the infrared spectrum. Said percentage has been found in practical measurements and reflects the typical amount of specular reflectivity on the total reflectance.

In a practical implementation for SpO2 estimation said processing unit is configured to compute the arterial blood oxygen concentration from said PPG signals by $$C_1 - C_2 \cdot \frac{AC_R/DC_R}{AC_{IR}/DC_{IR}} \cdot \frac{(1-S)}{1 - S \cdot DC_{IR}/DC_R}$$

wherein
$AC_R/DC_R$ is the normalized pulsatility at a wavelength in the red spectrum,
$AC_{IR}/DC_{IR}$ is the normalized pulsatility at a wavelength in the infrared spectrum,
$DC_R$ is the DC level of the PPG signals at a wavelength in the red spectrum,
$DC_{IR}$ is the DC level of the PPG signals at a wavelength in the infrared spectrum,
$C_1$ and $C_2$ are predetermined calibration constants and
S is an estimate of the relative specular reflection contained in the DC level of the PPG signals. Hence, the conventionally used calibration factor $C_2$ is multiplied with a correction factor $$\frac{(1-S)}{1 - S \cdot DC_{IR}/DC_R}.$$

This provides for a substantial improvement of accuracy of the SpO2 estimation.

In this embodiment it is preferred that a value in the range of 5% to 15%, in particular 10%, for S, which has been found in practical measurements and reflects the typical amount of specular reflectivity on the total reflectance.

Preferably, said signal extraction unit is configured to extract a first PPG signal at a wavelength in the red spectrum and a second PPG signal at a wavelength in the infrared spectrum. The use of such wavelengths has been shown to provide good results for the determined concentration of a substance in the subject's blood. For instance, a first PPG signal is determined at a first wavelength in the range from 550 to 780 nm and a second PPG signal is determined at a second wavelength in the range from 780 nm to 1000 nm.

Further, in an embodiment said detection signals are images of at least said skin area of the subject obtained by an imaging unit, in particular a white-balanced imaging unit, wherein the imaging unit forms a part of the system according to the present invention. The use of a white-balanced imaging unit, e.g. a white-balanced camera, provides that the influence of specular reflection can be removed or reduced. In particular, a white-balanced imaging unit provides the knowledge that the relative specular reflection is equally strong in all wavelength channels, and hence the influence can be reduced/removed.

In still a further aspect the present invention relates to a device for determining the concentration of a substance in the blood of a subject, comprising processing means configured to
receive detection signals reflected back from a skin area of the subject in response to irradiation of the skin area by a radiation signal,
extract at least two photo-plethysmography, PPG, signals at two different wavelengths from said detection signals, and
compute the concentration of a desired substance in the blood of the subject based on said PPG signals, wherein said computation is adapted to the skin tone of the subject.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
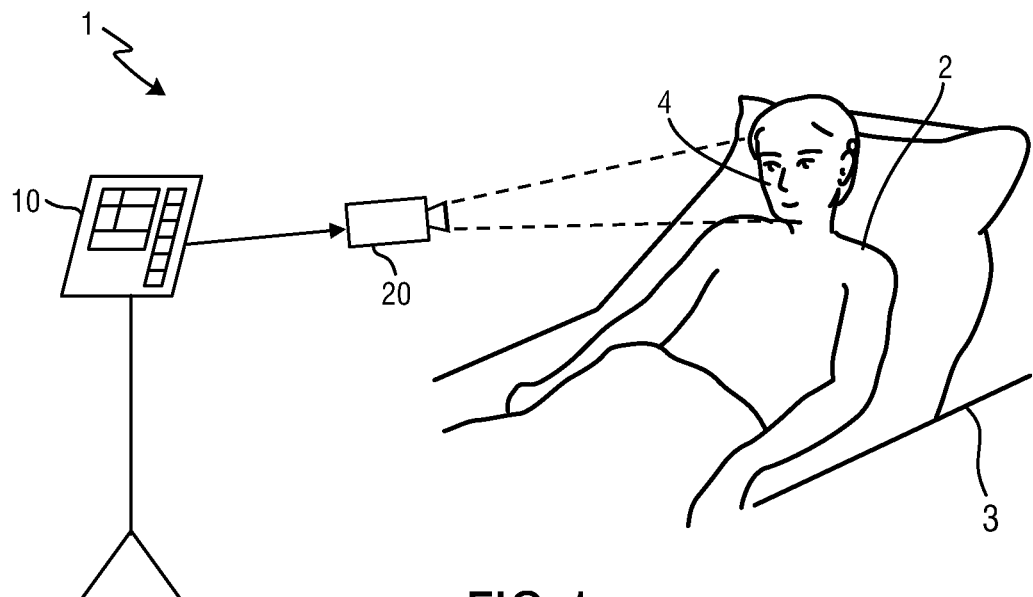
FIG. 1 shows a schematic diagram of a first embodiment of a system and device for determining the concentration of a substance in the blood of a subject.

FIG. 1 shows a schematic diagram of an embodiment of a system 1 and device 10 for determining the concentration of a substance in the blood of a subject 2. Hereinafter, the invention shall be explained by determining the oxygen saturation (SpO2) in the subject's blood. However, all explanations mutually apply for determining the concentration of other substances in the subject's blood, such as $CO_2$, CO, bilirubin, or potentially other gases, etc. Other substances may require the use of different wavelengths though. The subject 2 in this example is a patient lying in a bed 3, e.g. in a hospital or other healthcare facility, but may also be a neonate or premature infant, e.g. lying in an incubator, or person at home or in a different environment. Besides the device 10 the system 1 generally comprises a radiation detection unit 20 for detecting detection signals reflected back from a skin area 4 of the subject 2 in response to irradiation of the skin area 4 by a radiation signal.

In this example the radiation detection unit 20 is an imaging unit, in particular a camera (also referred to as detection unit or as camera-based or remote PPG sensor), for obtaining images of at least said skin area 4 of the subject 2 as detection signals. The skin area 4 is preferably an area of the face, such as the cheeks or the forehead, but may also be another area of the body, such as the hands or the arms. The radiation signal in this example is the ambient light, e.g. as provided by the sun and/or from room lighting. In other embodiment special light source(s) are provided for illuminating the subject 2 or at least the skin area 4 of the subject 2 with radiation of particular wavelength(s) and/or (only) at times of measurement (e.g. during nighttime).

The image frames captured by the camera may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color).

The image frames include at least some image pixels being representative of a skin portion of the subject. Thereby, an image pixel may correspond to one photosensitive element of a photo-detector and its (analog or digital) output or may be determined based on a combination (e.g. through binning) of a plurality of the photosensitive elements.

The obtained detection signals, i.e. in this embodiment the sequence of images, are provided to the device 10 for further processing that will be explained below in more detail.

While such a system can generally be used for obtaining various vital signs by use of the known remote PPG technology, it is used according to an embodiment of the present invention for determining the oxygen saturation of arterial blood (also referred to as SpO2) within the subject 2. The light reflected back from the skin of the subject is modulated by the pulsatile arteries and the modulation amplitude contains the information of the blood saturation levels. In known remote PPG systems, SpO2 is computed by measuring this PPG amplitude (caused by pulsatile blood in arteries) at two distinct wavelengths. The ratio between the PPG amplitudes (DC normalized) of the two wavelengths gives the equation 1 for the computation of SpO2:

$$SpO_2 = C_1 - C_2 \frac{R}{IR} \quad (1)$$

with $R = \frac{AC_{Red}}{DC_{Red}}$ and $IR = \frac{AC_{IR}}{DC_{IR}}$

Figure 2:
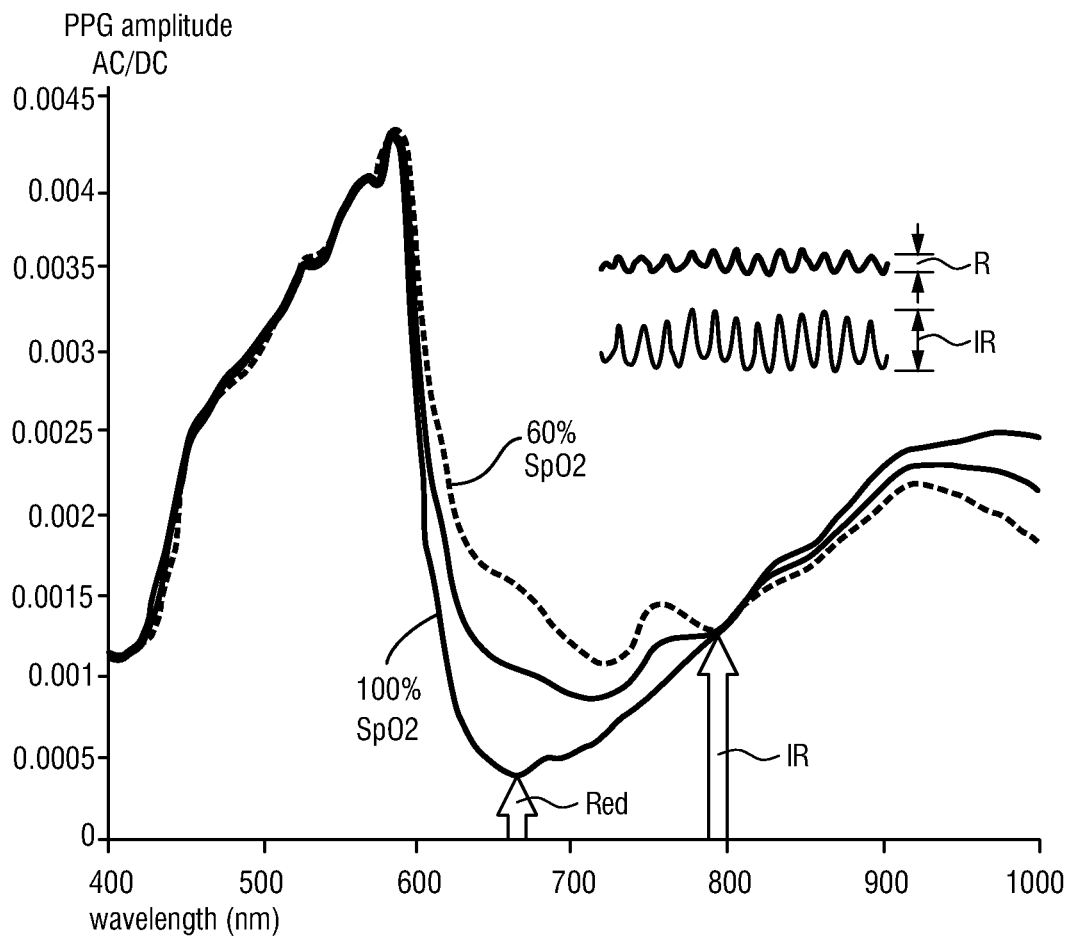
FIG. 2 shows a diagram of the PPG amplitude for various values of SpO2 over wavelength.

FIG. 2 shows a corresponding diagram of the PPG amplitude for various values of SpO2 over wavelength, The constants C1 and C2 in the equation above are called the calibration parameters (or calibration constants), which currently make up one of the biggest problems faced in SpO2 measurements in terms of calibration. Calibration refers to inter-person and intra-person calibration leading to incorrect SpO2 measurements and errors can be caused due to a number of factors. One of these causes has been found to be specular reflectance, the mirror like reflectance of light of the skin surface, which makes camera SpO2 measurement different from contact sensor based measurement.

Figure 3:
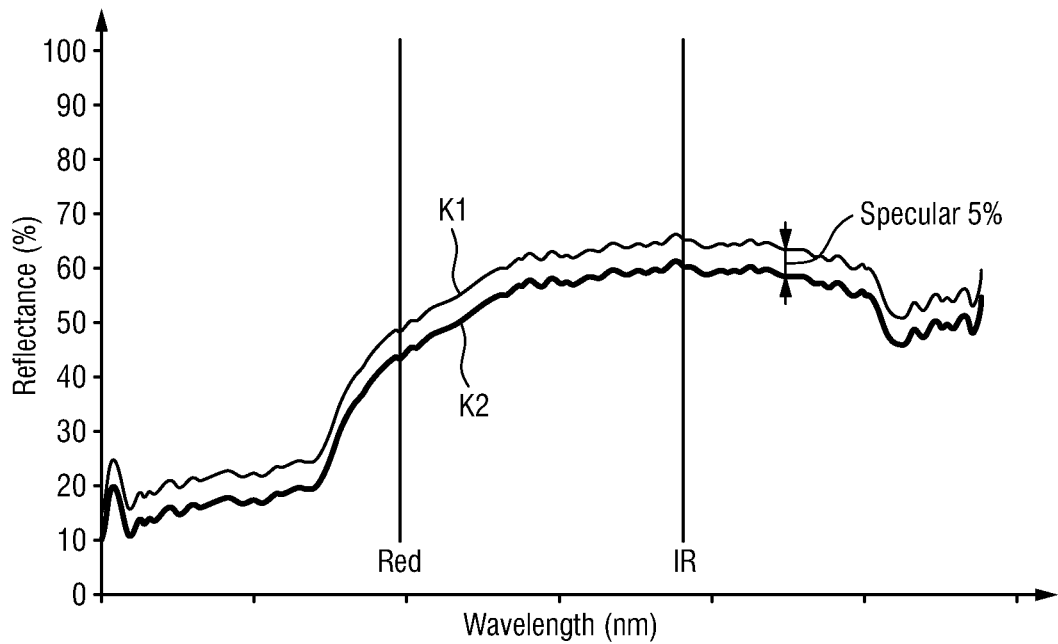
FIG. 3 shows a diagram illustrating the effect of specular reflectance.

Pulsatility only occurs in that fraction of the light that has penetrated into the skin and is diffusely reflected. The specularly reflected light reaching the camera 20 does not contain any light modulation due to arterial blood pulsatility and hence causes a decrease in relative pulsatility of the total reflected light. Consequently there will be errors in SpO2 measurement depending on the fraction of the specularly reflected light in the total reflected light from the skin. Specular reflectance depends on the angles between the camera, the subject and the illumination source and is an additive property adding an equal but unknown amount of DC reflectance across all wavelengths equally as shown in FIG. 3 depicting a curve K1 of the diffuse and specular reflectance and a curve K2 of the diffuse reflectance only, both curves over wavelengths of light.

The effect of specular reflectance can be shown with a simple computation as shown in the following table.

| | DC Red | DC IR | AC Red Pulsatility = 0.1 | AC IR Pulsatility = 0.2 | RR $\frac{AC_{red}/DC_{red}}{AC_{ir}/DC_{ir}}$ | SpO2 C1 = 123 C2 = 54 |
|---|---|---|---|---|---|---|
| Without Specular reflectance (Ideal conditon) | 0.4 | 0.55 | 0.04 | 0.11 | 0.5 | 96 |
| With Specular reflectance (+5%) | 0.45 | 0.6 | 0.04 | 0.11 | 0.4848 | 96.82 |

Since the additive specular reflectance seen by the camera does not contain any modulated light the AC component for the wavelengths remains constant. This causes an overall change in the double ratio leading to a slightly different SpO2 and hence a different calibration constant. This effect gets magnified based on the relative difference between the reflectance for the two wavelengths. A higher reflectance of the numerator (i.e. for the wavelength of red light) with respect to the denominator (i.e. for the wavelength of IR light) leads to a lower SpO2 (and hence a higher C1 to compensate) and vice versa.

Figure 4:
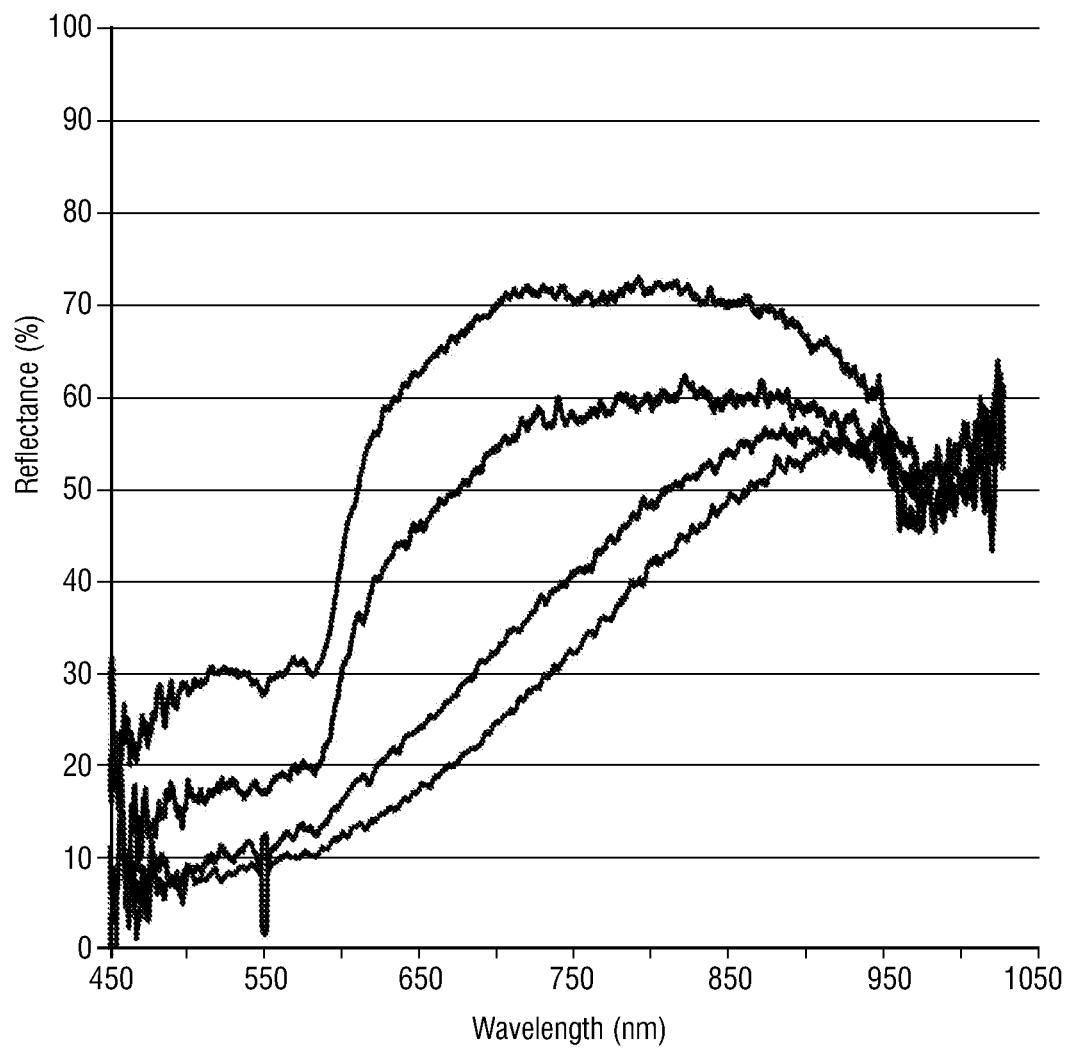
FIG. 4 shows a diagram showing reflectance measurements for different subjects.

Should the diffuse reflectance of the skin be identical in the red and the infrared wavelength range, the effect of specular reflectance on the numerator and the denominator becomes identical and the effect of the specular reflection absent. However, as shown in FIG. 4 depicting a diagram showing reflectance measurements for four different subjects, the reflection can be very differently between the wavelengths, particularly for subjects with a dark skin-tone. Consequently, even a constant specular reflection will lead to a calibration that strongly depends on the skin-tone of the subject. Particularly, subjects with a very dark skin can have significantly stronger absorption of the red compared to the infrared.

One solution to reduce or remove this effect is the use of cross-polarization. The polarizers are attached at the illumination source and the cameras and oriented in such a way that all specularly reflected light is blocked away. Even though this is a generic solution, one key problem lies in the low practicality of this solution. To start with, unpolarized ambient light has to be eliminated from the scene. Furthermore, large illumination sources, as currently being used, require large polarization sheets of high quality. Further, such a large illumination source does not allow the polarization planes to be normal with respect to the camera-subject source geometry, a condition necessary for the complete removal of specular reflectance. This then necessitates the use of different illumination sources which might not be very practical.

Hence, the present invention substantially adapts the calibration to the recorded skin-tone of the subject. This adaption is based on the above explained recognition that the specular reflection causes the calibration to be different for subjects with different skin-tones.

Figure 5:
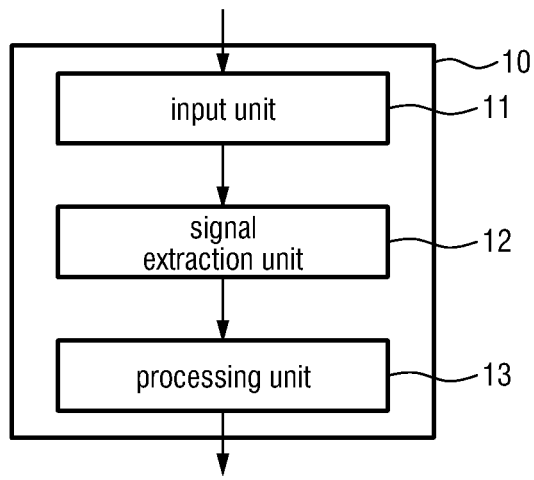
FIG. 5 shows a schematic diagram of a device according to the present invention.

An embodiment of a corresponding device 10 according to the present invention is schematically shown in FIG. 5. The device 10 comprises an input unit 11 for receiving detection signals reflected back from a skin area of the subject in response to irradiation of the skin area by a radiation signal, a signal extraction unit 12 for extracting at least two photo-plethysmography (PPG) signals at two different wavelengths from said detection signals, and a processing unit 13 for computing the concentration of a desired substance in the blood of the subject based on said PPG signals, wherein said computation is adapted to the skin tone of the subject.

Detection signals received at input unit 11 are preferably obtained by an imaging unit such as a camera (not further shown) for obtaining images of at least said skin area of the subject as detection signals.

A "signal extraction unit" for extracting a PPG signal from a detection signal, such as provided by a set of image frames, may particularly correspond to an analog or digital signal processor. A PPG signal may particularly correspond to a signal representing fluctuations in the light intensity determined based on a time series of image frames. Such a PPG signal may be representative of a vital sign of a subject such as a heart rate, the respiratory rate or the blood oxygen saturation. A signal extraction unit may particularly extract a PPG signal based on multiple image pixels and/or based on a series of time-consecutive image frames comprised in a detection signal. The extraction of PPG signals from an imaging unit is widely known in the art of vital signs monitoring and remote PPG.

A "processing unit" or "processor" as used herein encompasses a component for processing, for example, those that process in response to a signal or data and/or those that process autonomously. A processing unit should be understood to encompass microprocessors, microcontrollers, programmable digital signal processors, integrated circuits, computer software, computer hardware, electrical circuits, application specific integrated circuits, programmable logic devices, programmable gate arrays, programmable array logic, personal computers, chips, and any other combination of discrete analog, digital, or programmable components, or other devices capable of providing processing functions.

Preferably, for image acquisition a white-balanced camera is used so that the relative reflection at the two wavelengths can be known alternatively and a separate measurement of the skin-reflectance of the subject is also possible. With such a setup, it is possible to try to eliminate the specular reflection from the DC-terms in the ratio-of ratios used for calculating SpO2 as shown above. The exact value of the specular reflection cannot be known, but a very reasonable guess turns out to be possible if (after performing a white-balancing of the camera prior to the measurements) it is assumed that the reflection in the infrared wavelength range is not very much depending on skin-tone.

Referring to FIG. 3 the (on average reasonable) assumption is made that the skin-reflectance at the infrared wavelength is around 50% regardless of the skin-tone of the subject. Further, it is assumed (e.g. based on measurements with and without polarizers) that a reasonable estimate of the relative specular reflection, S, is around 5%, or consequently 10% of the total infrared skin reflection. Knowing that the camera used for image acquisition has been white-balanced, the DC levels of red and infrared wavelength ranges can consequentially be corrected by subtracting equal amounts of specular reflection (e.g. S=10; generally S being in the range from 5 to 15) from the DC levels of both channels.

If the assumptions are reasonable, the effect of specular reflection on the normalization can be almost eliminated, and if they are a bit off, the effect of the specular reflection on the SPO2 measurement can still be largely reduced.

The modified SPO2 equation suggested according to this embodiment of the present invention is as follows:

$$SpO_2 = C_1 - C_2 \frac{AC_R/DC'_R}{AC_{IR}/DC'_{IR}} \qquad (2)$$

with DC being the actually measured DC values from the image data and DC' being the DC values without specular reflectance. With the assumptions of specular reflectance, $DC'_{IR} \to (1-S) \cdot DC_{IR}$ and $DC'_R \to DC_R - S \cdot DC_{IR}$ it holds:

$$\begin{aligned} SpO_2 &= C_1 - C_2 \cdot \frac{AC_R/(DC_R - S \cdot DC_{IR})}{AC_{IR}/(1-S)DC_{IR}} \\ &= C_1 - C_2 \cdot \frac{AC_R}{AC_{IR}} \cdot \frac{1/(DC_R - S \cdot DC_{IR})}{1/(1-S)DC_{IR}} \\ &= C_1 - C_2 \cdot \frac{AC_R}{AC_{IR}} \cdot \frac{(1-S) \cdot DC_{IR}}{DC_R - S \cdot DC_{IR}} \\ &= C_1 - C_2 \cdot \frac{AC_R}{AC_{IR}} \cdot \frac{(1-S)}{DC_R/DC_{IR} - S} \end{aligned}$$

Multiply and divide by $DC_{IR}/DC_R$ to get to the form of equation (2)

$$\begin{aligned} &= C_1 - C_2 \cdot \frac{AC_R/DC_R}{AC_{IR}/DC_{IR}} \cdot \frac{(1-S)}{1 - S \cdot DC_{IR}/DC_R} \\ &= C_1 - C'_2 \cdot \frac{AC_R/DC_R}{AC_{IR}/DC_{IR}} \end{aligned}$$

Where the calibration constant, $C_2$, of eq. (1) is adapted to:

$$C'_2 = C_2 \cdot \frac{(1-S)}{1 - S \cdot DC_{IR}/DC_R} \qquad (3)$$

It should be noted, however, that alternatives exist to adapt the equation to the skin-tone of the subject. One alternative would be to measure the skin-tone of the subject with another device/sensor, e.g. a skin-tone analyzer that provides a melanin-index. This melanin-index could then be used to adapt the SpO2 value using a look-up-table or another function.

Further, by use of the present invention other concentrations could be corrected in a similar way, either using the DC reflections of the skin as available from the camera, or using a separate sensor. In this case the basic equation (1) may be different, and it may be advantageous to use other wavelengths. For instance, for determining bilirubin it would be useful to use visible light with a wavelength around 475 nm (blue light).

The above assumptions have been approved by corresponding test measurements. These measurements have also shown that the white-balancing of the camera could in principle be eliminated if the illumination of the light source (used for illuminating the skin area from which the PPG signals are derived) is separately measured with a set of two photo-diodes (red and infrared sensitive respectively) or a measurement device like the spectrophotometer. Further, it was recognized that compensation is possible without white-balancing the camera, as long as the relative gains of the red and infrared channels are not changed, and the spectrum of the light source remains the same.

The main application of the present invention is the measurement of contactless SpO2 robust to the presence of specular reflectance and/or motion for patient monitoring applications in the NICU and general ward. The present invention is equally applicable for contact vital signs sensors and remote (camera-based) PPG systems, and can also be used to determine the concentration of other substances in the subject's blood, such as CO2, CO, or bilirubin.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for determining a concentration of a substance in blood of a subject, comprising:
an input unit configured to receive detection signals indicative of radiation reflected back from a skin area of the subject in response to irradiation of the skin area,
a signal extraction unit configured to extract at least two photo-plethysmography, PPG, signals at two different wavelengths from the detection signals, and
a processing unit configured to obtain skin tone information indicative of a skin tone of the subject and compute the concentration of a desired substance in the blood of the subject based on the PPG signals, wherein the processing unit is further configured to compensate the computation for the skin tone of the subject based on the skin tone information, wherein the processing unit is further configured to at least one of:
use as a correction factor for correcting the denominator of the first normalized pulsatility at a wavelength in the red spectrum a fraction of the DC level of the PPG signal at a wavelength in the infrared spectrum,
use as a correction factor a fraction in the range of 5% to 15% of the DC level of the PPG signal at a wavelength in the infrared spectrum; and
compute arterial blood oxygen concentration from the PPG signals by $$C_1 - C_2 \cdot \frac{AC_R/DC_R}{AC_{IR}/DC_{IR}} \cdot \frac{(1-S)}{1 - S \cdot DC_{IR}/DC_R}$$

where
$AC_R/DC_R$ is the normalized pulsatility at a wavelength in the red spectrum,
$AC_{IR}/DC_{IR}$ is the normalized pulsatility at a wavelength in the infrared spectrum,
$DC_R$ is the DC level of the PPG signals at a wavelength in the red spectrum,
$DC_{IR}$ is the DC level of the PPG signals at a wavelength in the infrared spectrum,
$C_1$ and $C_2$ are predetermined calibration constants, and
S is an estimate of the relative specular reflection contained in the DC level of the PPG signals.

2. The device as claimed in claim 1,
wherein the processing unit is further configured to form a ratio of a first normalized pulsatility at a first wavelength and a second normalized pulsatility at a second wavelength for the computation of the concentration, wherein the denominator of the first and/or the second normalized pulsatility is corrected by a correction factor.

3. The device as claimed in claim 1,
wherein the processing unit is configured to use a value in the range of 5% to 15% for S.

4. The device as claimed in claim 1, further including: a non-contact remote photoplethysmography (rPPG) camera configured to generate images of the skin area of the subject.

5. The device as claimed in claim 4,
wherein the processing unit is further configured to adapt the computation to an average intensity of the radiation reflected back from the skin area at the two different wavelengths.

6. A device for determining a concentration of a substance in blood of a subject, comprising:
an input unit configured to receive detection signals reflected back from a skin area of the subject in response to irradiation of the skin area by a radiation signal,
a signal extraction unit configured to extract at least two photo-plethysmography, PPG, signals at two different wavelengths from the detection signals, and
a processing unit configured to compute the concentration of a desired substance in the blood of the subject based on said PPG signals, wherein the computation is adapted to the skin tone of the subject,
wherein the processing unit is configured to form a ratio of a first normalized pulsatility at a first wavelength and a second normalized pulsatility at a second wavelength for the computation of the concentration, wherein the denominator of the first and/or the second normalized pulsatility is corrected by a correction factor,
wherein the correction factor is used for correcting the denominator of the first normalized pulsatility a fraction of a first DC level of the PPG signal at the second wavelength and/or is used for correcting the denominator of the second normalized pulsatility a fraction of a second DC level of the PPG signal at the first wavelength.

7. A system for determining a concentration of a target substance in the blood of a subject, comprising:
a photoplethysmography (PPG) detector configured to detect radiation in a red spectrum and an infrared spectrum reflected back from a skin area of the subject in response to irradiation of the skin area and generate detection signals indicative thereof, and
a computer processor configured to determine the concentration of the target substance in the blood corrected for a skin tone of the subject from the detection signals including:
receiving the detection signals from the PPG detector,
extracting PPG signals in the red spectrum and in the infrared spectrum from the detection signals, and
computing the concentration of the target substance based on the PPG signals, including:
computing a ratio of a normalized pulsatility in the red spectrum and the infrared spectrum, and
using a correction factor for correcting a denominator of the ratio of the normalized pulsatility in the red spectrum with a fraction of a DC level of the PPG signal in the infrared spectrum.

8. The system as claimed in claim 7,
wherein the PPG detector includes a remote PPG (rPPG) camera configured to obtain images of the skin area of the subject; and
a display configured to display the determined concentration.

9. A method for determining a concentration of a selected substance in the blood of a subject, comprising:
receiving detection signals indicative of radiation reflected back from a skin area of the subject in response to irradiation of the skin area,
extracting at least two photo-plethysmography (PPG) signals at wavelengths in a red spectrum and in an infrared spectrum from the detection signals, and
computing the concentration of the selected substance in the blood of the subject based on the PPG signals compensated for a skin tone of the subject, the computing including:
computing the arterial blood oxygen concentration from the PPG signals by $$C_1 - C_2 \cdot \frac{AC_R/DC_R}{AC_{IR}/DC_{IR}} \cdot \frac{(1-S)}{1-S \cdot DC_{IR}/DC_R}$$

where
$AC_R/DC_R$ is a normalized pulsatility at the wavelength in the red spectrum,
$AC_{IR}/DC_{IR}$ is a normalized pulsatility at the wavelength in the infrared spectrum,
$DC_R$ is the DC level of the PPG signals at the wavelength in the red spectrum,
$DC_{IR}$ is the DC level of the PPG signals at the wavelength in the infrared spectrum,
$C_1$ and $C_2$ are predetermined calibration constants, and
S is an estimate of the relative specular reflection contained in the DC level of the PPG signals.

10. A computer readable non-transitory medium having instructions stored thereon which, when carried out on a computer, cause the computer to perform the steps of the method as claimed in claim 9.

11. A device for determining a concentration of a substance in the blood of a subject, comprising a computer processor configured to:
receive detection signals indicative of radiation reflected back from a skin area of the subject,
extract at least two photo-plethysmography (PPG) signals at two different wavelengths from the detection signals, and
compute the concentration of a desired substance in the blood of the subject based on the PPG signals corrected for a skin tone of the subject, including:
computing a ratio of a first normalized pulsatility at a first wavelength and a second normalized pulsatility at a second wavelength for the computation of the concentration, and
correcting a denominator of the ratio of the first and the second normalized pulsatility with a correction factor, wherein the correction factor at least one of:
corrects the denominator of the ratio of the first and normalized pulsatility by a fraction of a DC level of the PPG signal at one of the first and second wavelengths,
corrects the denominator of the ratio of the first normalized pulsatility at a wavelength in the red spectrum a fraction of a DC level of the PPG signal at a wavelength in an infrared spectrum, and
includes a fraction in a range of 5% to 15% of a DC level of the PPG signal at a wavelength in the infrared spectrum.

12. The device as claimed in claim 11, further including:
a remote PPG camera configured to receive radiation reflected back from the skin area of the subject and generate the detection signals, and
at least one of a display device configured to display the computed concentration and a computer memory configured to store the computed concentration.

13. A device for determining an arterial blood oxygen of a subject, comprising a computer processor configured to:
receive detection signals indicative of radiation reflected back from a skin area of the subject,
extract at least two photo-plethysmography (PPG) signals at two different wavelengths from the detection signals,
correct the PPG signals for a skin tone of the subject, and
compute the arterial blood oxygen concentration from the PPG signals by:

$$C_1 - C_2 \cdot \frac{AC_R/DC_R}{AC_{IR}/DC_{IR}} \cdot \frac{(1-S)}{1 - S \cdot DC_{IR}/DC_R}$$

where
$AC_R/DC_R$ is the normalized pulsatility at a wavelength in the red spectrum,
$AC_{IR}/DC_{IR}$ is the normalized pulsatility at a wavelength in the infrared spectrum,
$DC_R$ is the DC level of the PPG signals at a wavelength in the red spectrum,
$DC_{IR}$ is the DC level of the PPG signals at a wavelength in the infrared spectrum,
$C_1$ and $C_2$ are predetermined calibration constants, and
S is an estimate of the relative specular reflection contained in the DC level of the PPG signals.

14. The device as claimed in claim 13,
wherein S is a value in a range of 5% to 15%.

* * * * *